Sept. 2, 1947. R. H. KING Plant Pat. 759
NECTARINE PLANT
Filed Nov. 12, 1946
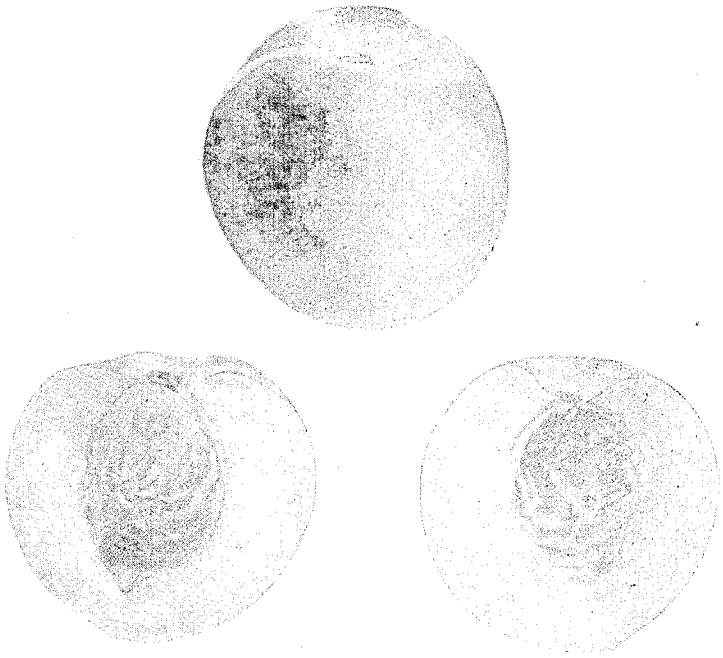
Inventor
R. H. King
By Robb & Robb
Attorneys Patented Sept. 2, 1947

Plant Pat. 759

UNITED STATES PATENT OFFICE

759

NECTARINE PLANT

Richard H. King, Sheffield, Ala., assignor to Stark Bros. Nurseries and Orchards Company, Louisiana, Mo., a corporation of Missouri Application November 12, 1946, Serial No. 709,148

1 Claim. (Cl. 47—62)

The present discovery relates to a new and distinct variety of nectarine plant, originating as a seedling of Burbank's "Flaming-Gold" variety of fuzzless peach or nectarine.

The Burbank variety is notable for its smooth, waxy skin of flashing gold blending into flaming red coloring, its delicious peach flavor and golden orange, juicy flesh.

The present variety resembles this Burbank nectarine very closely in appearance, size and flavor, but is dominantly distinguished therefrom by its early ripening period at least two weeks ahead of Burbank, when grown under comparable conditions.

Asexual reproduction shows that these characteristics hold true through succeeding propagations.

The drawing illustrates specimens of this new variety both in elevation and sectional views, depicting also the pit and its cavity.

The following is a detailed description of the new variety, giving color designations according to the conventional dictionary definition of terminology as well as corresponding color terms according to Ridgway's Color Standard:

Dates first and last picking—July 27, 1946—August 5, 1946.

Tree: Large; vigorous; dense; spreading; vase formed; hardy; very productive; regular bearer.

*Trunk.*—Stocky; medium smooth.

*Branches.*—Medium stocky; smooth; Dull Brown (Ridgway, Liver Brown, Plate XIV, Color 7′, Tone M); red, glossy twigs. *Lenticels*—medium number; medium size.

*Leaves.*—Length, 5¾″; width, 1⅜″. Large; ovate; acutely pointed; medium thick; smooth; Dark Green (Ridgway, Dark Yellowish Green, Plate XVIII, Color 33′, Row M). *Margin*—finely serrate. *Petiole*—medium length; thick. *Glands*—average number, 3 to 5; alternate; medium size; reniform; free.

*Flowers.*—Dates first and full blossoms—March 27, 1946—March 30, 1946. Medium early compared with other varieties; medium size; Pink.

Fruit: Maturity when described—eating, July 28, 1946.

*Size.*—Uniform; medium size. Axial diameter—2¼″. Transverse in suture plane—2¼″. At right angles to suture plane—2⅛″.

*Form.*—Uniform; symmetrical; globose; oblong; sides equal. *Suture*—distinct; extends from base to apex; has slight depression beyond pistil point. *Ventral surface*—rounded; slightly lipped toward apex. Lips—unequal. *Cavity*—rounded; circular; elongated in suture plane with suture showing on one or both sides on some specimens. Depth—⅜″; breadth—⅞″. *Base* — truncate. *Apex* — apical. *Stem*—length, ¼″; stout. Adherence to stone—strong. *Skin*—thin; tough; tenacious to flesh. Tendency to break—none. Color—highly blushed red (Ridgway, Bordeaux, Plate XII, Color 71, Tone K). Down—wanting.

*Flesh.*—Color—Yellow (Ridgway, Primuline Yellow, Plate XVI, Color 19′). Surface of pit—Yellow. *Texture*—firm. *Fibres*—abundant; tender. *Ripens*—Fairly even. *Flavor*—Subacid. *Aroma*—distinct. *Eating quality*—best.

*Stone.*—Semi-free. Adheres to flesh over upper half of sides. *Fibres*—long. *Size*—medium. Length 1¼″. Thickness ¾″. *Form*—obovoid; full toward base. *Base*—straight. *Hilum*—narrow; oval. *Apex*—acute. *Sides*—equal on right and left sides. *Surface*—regularly furrowed throughout; pitted toward base. *Ridges*—rounded toward apex. *Pits*—circular. Ventral edge—thick, without wing. *Dorsal edge*—Full with deep narrow groove throughout. Ridges on either side—interrupted.

Use: Market; Dessert.

Keeping quality: Medium.

Resistance to: Insects and diseases—good.

Shipping quality: Good.

I claim:

A new and distinct variety of nectarine plant, characterized by its similarity in appearance, size and flavor to Burbank's "Flaming-Gold" nectarine, while differing therefrom by its earlier ripening period, substantially as shown and described.

RICHARD H. KING.